US007955384B2

(12) United States Patent
Rafiee et al.

(10) Patent No.: US 7,955,384 B2
(45) Date of Patent: Jun. 7, 2011

(54) CORONARY SINUS APPROACH FOR REPAIR OF MITRAL VALVE REGURGITATION

(75) Inventors: Nasser Rafiee, Andover, MA (US); Nareak Douk, Lowell, MA (US); James F. Crittenden, Hollis, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1290 days.

(21) Appl. No.: 10/531,833

(22) PCT Filed: Nov. 11, 2004

(86) PCT No.: PCT/US2004/038004
§ 371 (c)(1),
(2), (4) Date: Sep. 25, 2006

(87) PCT Pub. No.: WO2005/046530
PCT Pub. Date: May 26, 2005

(65) Prior Publication Data
US 2007/0010878 A1    Jan. 11, 2007

Related U.S. Application Data

(60) Provisional application No. 60/519,115, filed on Nov. 12, 2003.

(51) Int. Cl.
*A61F 2/24* (2006.01)
(52) U.S. Cl. .................. 623/2.11; 623/2.36; 623/2.37
(58) Field of Classification Search .............. 623/2.11, 623/2.36–2.37
See application file for complete search history.

(56) References Cited

U.S. PATENT DOCUMENTS

| | | | | | |
|---|---|---|---|---|---|
| 3,108,593 | A | * | 10/1963 | Glassman | 606/127 |
| 5,059,193 | A | * | 10/1991 | Kuslich | 606/247 |
| 5,171,278 | A | * | 12/1992 | Pisharodi | 128/898 |
| 5,454,365 | A | * | 10/1995 | Bonutti | 600/204 |
| 5,752,969 | A | * | 5/1998 | Cunci et al. | 606/167 |
| 5,800,526 | A | * | 9/1998 | Anderson et al. | 623/1.16 |
| 6,086,605 | A | * | 7/2000 | Barbut et al. | 606/200 |
| 6,096,054 | A | * | 8/2000 | Wyzgala et al. | 606/170 |
| 6,210,432 | B1 | * | 4/2001 | Solem et al. | 623/1.15 |
| 6,443,959 | B1 | * | 9/2002 | Beland et al. | 606/127 |
| 7,011,682 | B2 | * | 3/2006 | Lashinski et al. | 623/2.37 |
| 7,473,274 | B2 | * | 1/2009 | Sater | 623/2.37 |
| 2002/0151970 | A1 | * | 10/2002 | Garrison et al. | 623/2.11 |
| 2002/0183836 | A1 | | 12/2002 | Liddicoat et al. | |
| 2002/0183838 | A1 | | 12/2002 | Liddicoat et al. | |
| 2002/0183841 | A1 | | 12/2002 | Cohn et al. | |
| 2003/0055495 | A1 | * | 3/2003 | Pease et al. | 623/2.11 |
| 2003/0105520 | A1 | * | 6/2003 | Alferness et al. | 623/2.36 |
| 2003/0212453 | A1 | | 11/2003 | Mathis et al. | |
| 2004/0249452 | A1 | * | 12/2004 | Adams et al. | 623/2.36 |
| 2004/0260317 | A1 | * | 12/2004 | Bloom et al. | 606/151 |

FOREIGN PATENT DOCUMENTS

| | | |
|---|---|---|
| WO | WO 02/091908 | 11/2002 |
| WO | WO 02/096275 | 12/2002 |
| WO | WO 2005/046530 A1 * | 5/2005 |

* cited by examiner

*Primary Examiner* — Paul Prebilic

(57) ABSTRACT

A device and method for treating cardiac valve regurgitation. The device includes a tubular member including a lumen there through and a locking mechanism and a compression device carried on the tubular member. The compression device is transformable to a compression configuration in response to axial displacement and is locked in the compression configuration by the locking mechanism. The method includes positioning the compression device adjacent a cardiac valve and applying an axial displacement to the compression device to transform the compression device into a compression configuration and locking the compression device in the compression configuration to apply a compressive force to the cardiac valve.

10 Claims, 8 Drawing Sheets

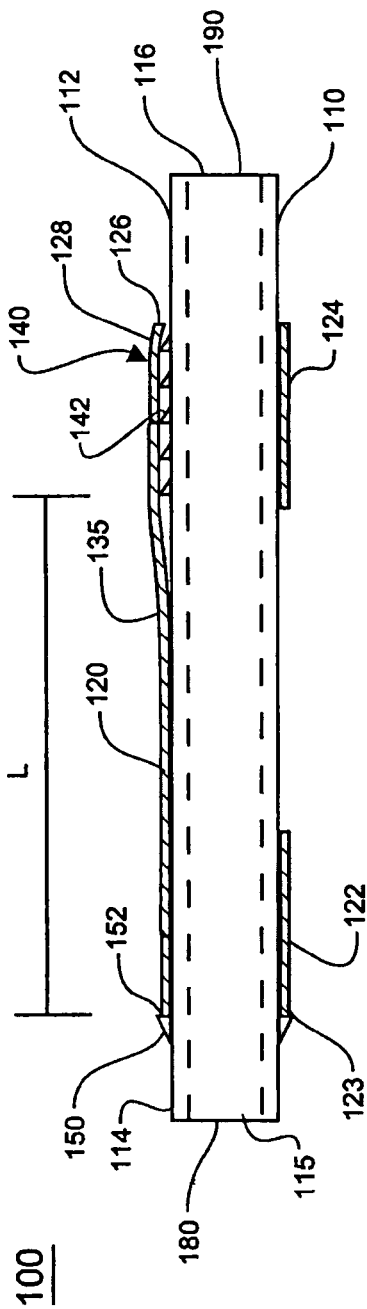
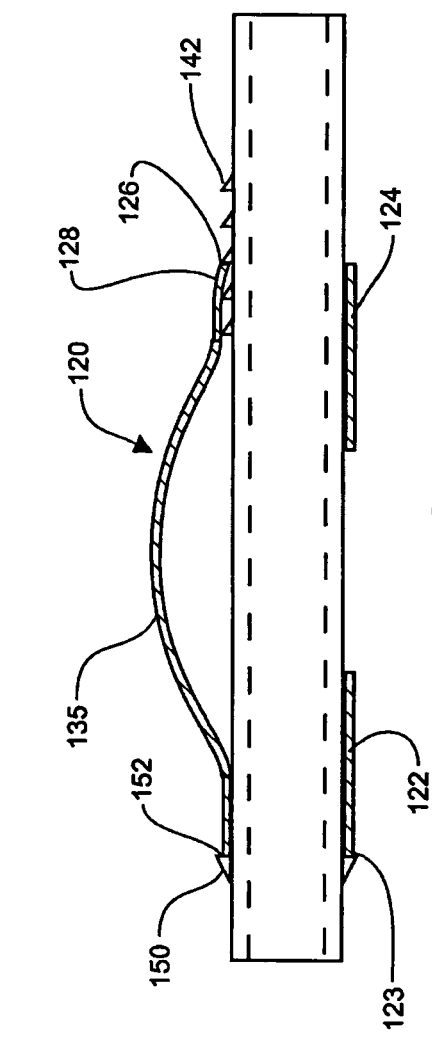

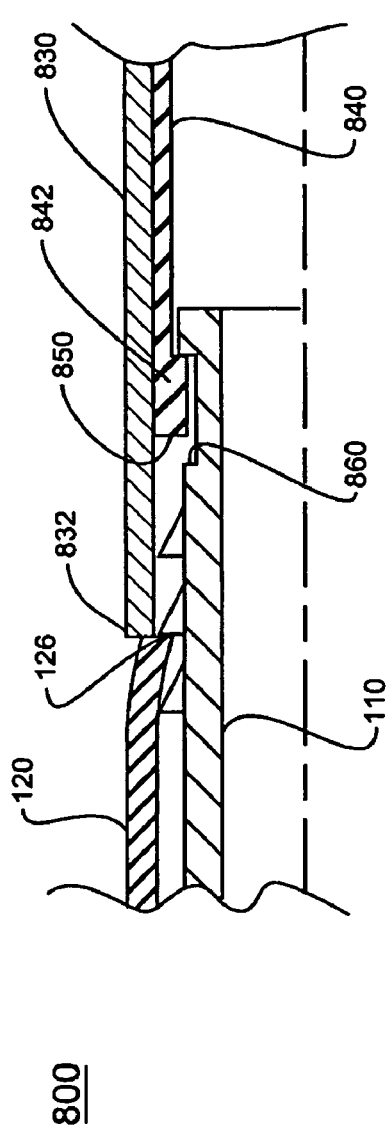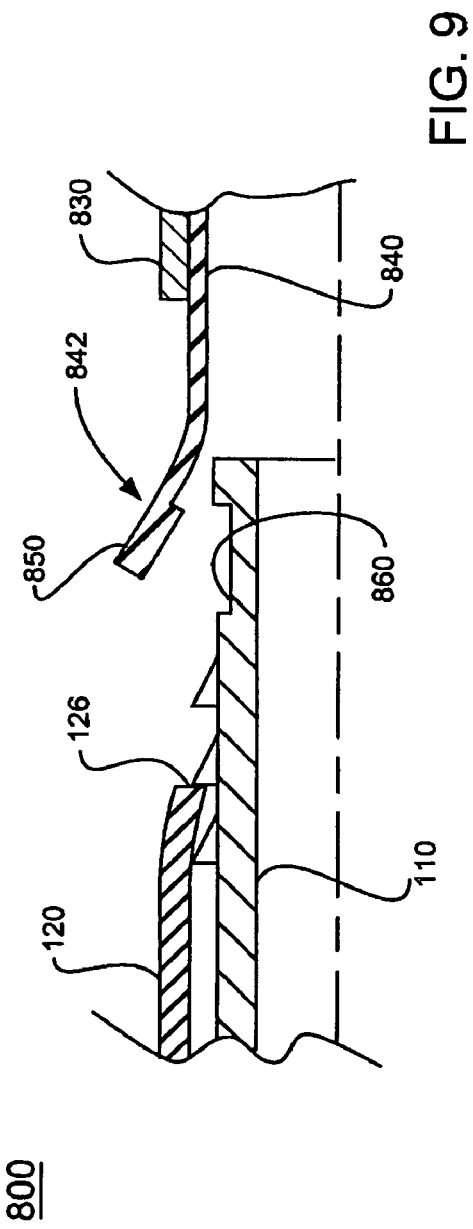

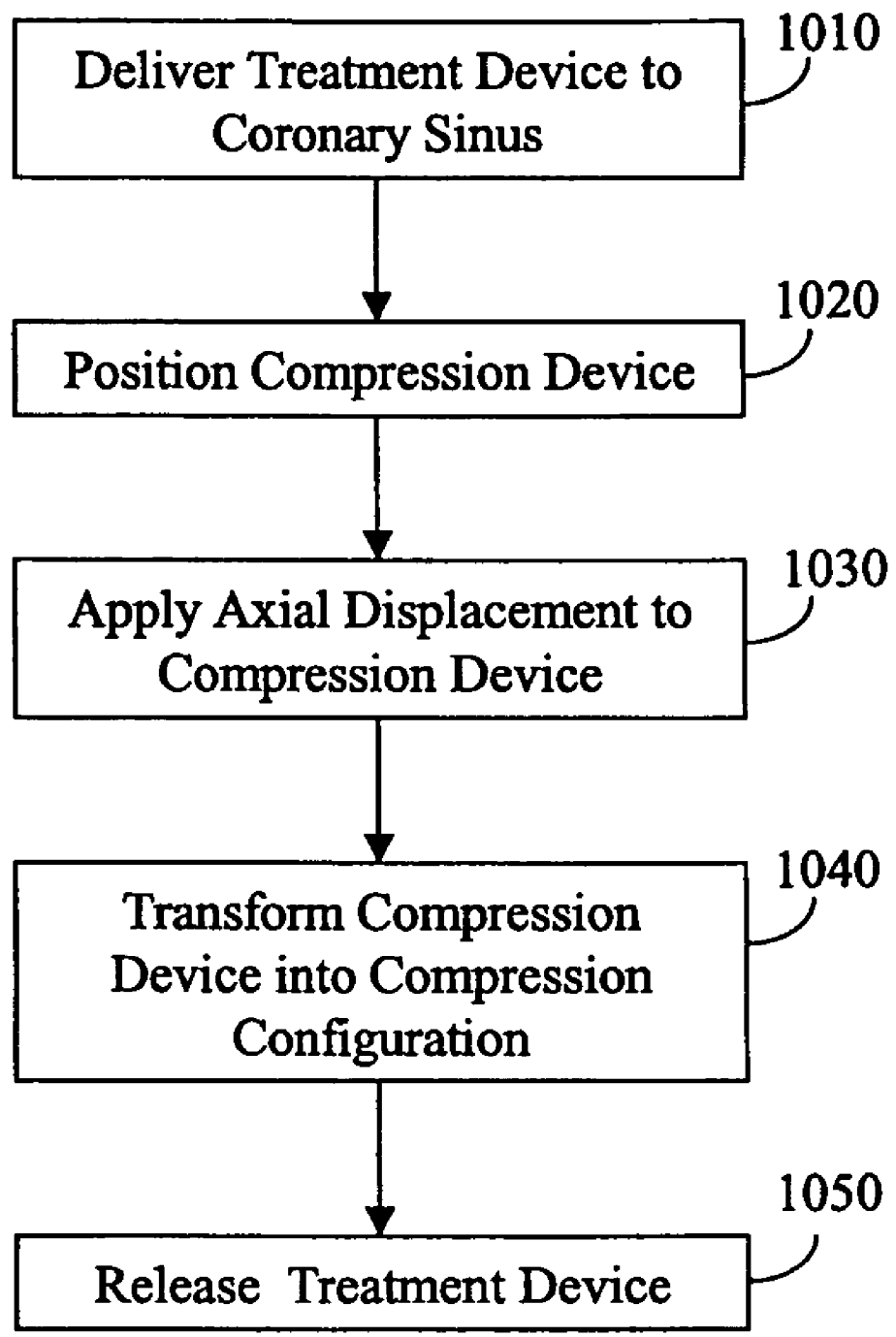

CORONARY SINUS APPROACH FOR REPAIR OF MITRAL VALVE REGURGITATION

TECHNICAL FIELD

The technical field of this disclosure is medical devices, particularly for treating mitral valve regurgitation.

BACKGROUND OF THE INVENTION

Valve insufficiency and regurgitation is a potentially grave health issue that can lead to cardiac dysfunction. Mitral valve insufficiency may comprise a valve that does not completely shut and affect the seal between the left ventricle and the left atrium. Historically, such a condition necessitated surgical intervention.

Surgical repair of mitral valve insufficiency historically involved the use of a sternotomy or a similar invasive procedure. After performing a sternotomy, the patient's heart would be stopped while the surgeon transected the chambers of the heart to gain access to the mitral valve. Upon attaining access to the mitral valve, the surgeon could then repair the valve by an annuloplasty, or suturing the valve. These procedures are complex, time consuming, and involve many risks attendant with open cardiac surgery. Complications may occur, and recovery time may be significant.

Catheter based valve replacement has been proposed as a way to avoid open-heart surgery. Such procedures involve excision of the native valve and replacement of the native valve with a prosthetic valve, or installation of a prosthetic valve over the native valve, or a device to repair the damaged valve. Previous proposed treatments involve the use of clips to bind the posterior and anterior leaflets of the mitral valve. To avoid cardiopulmonary bypass, the catheter based valve replacement is performed on a beating heart. Following excision of the native valve, no valve is present to preserve the pumping action of the heart while the permanent prosthetic valve is being implanted.

An additional consideration in both open-heart and catheter based valve replacement is the healing process after the prosthetic valve is implanted. After the surgical valve replacement procedure, scar tissue must form around the sewing cuff to secure the prosthetic valve in position. In current practice, multiple knotted sutures anchor the prosthetic valve in place until in-growth of scar tissue into the sewing cuff takes over the load bearing function. However, the placement of knotted sutures through a catheter can be very difficult and time consuming.

Artificial heart valves for temporary use are known in the art, but present certain problems. Some designs are complex, requiring alternating the inflation and deflation of balloons to alternately block and permit flow. Such designs require complex sensing and control systems. Other designs fail to provide access for tools that must reach the valve site for removal of the native valve and placement of the prosthetic valve. Yet other designs require elaborate supporting frames to hold the valve portion.

Alternative procedures to effect cardiac valve regurgitation involve the implantation of a device into the coronary sinus near the mitral valve. Some of these devices attempt to correct mitral valve regurgitation by placing a compressive force on the coronary sinus that then compresses at least a portion of the mitral valve annulus adjacent the coronary sinus. The resultant reduction in annulus radius brings the valve leaflets closer together to decrease the valve regurgitation. Still other devices that are implanted in the coronary sinus attempt to decrease valve regurgitation by straightening the radius of the coronary sinus. Straightening the coronary sinus results in a corresponding straightening of a portion of the mitral valve annulus adjacent the straightened coronary sinus. The intended result is to draw the valve leaflets closer together to decrease the valve regurgitation. One drawback to these implanted devices is that the size and shape of these devices often impede the flow of blood through the coronary sinus.

It would be desirable, therefore, to provide an apparatus and method for reducing cardiac valve regurgitation that overcomes these and other disadvantages.

SUMMARY OF THE INVENTION

One embodiment of the invention provides a system for treating cardiac valve regurgitation. The system includes a delivery catheter, a treatment device disposed within a lumen of the delivery catheter, a release mechanism releasably connected to the treatment device and a push tube slidably disposed within the delivery catheter for applying an axial force to the treatment device.

A second embodiment of the invention provides a device for treating cardiac valve regurgitation. The device comprises a tubular member having a lumen there through and having a locking mechanism and a compression device carried on the tubular member. The compression device is transformable to a compression configuration responsive to application of an axial force and is locked in the compression configuration with the locking mechanism.

Another embodiment of the invention provides a method for treating mitral valve regurgitation. The method comprises positioning a compression device within a coronary sinus adjacent a cardiac valve via a delivery catheter, applying an axial force to the compression device, transforming the compression device into a compression configuration responsive to the axial force and locking the compression device in the compression configuration to apply a compressive force to the cardiac valve.

The present invention is illustrated by the accompanying drawings of various embodiments and the detailed description given below. The drawings should not be taken to limit the invention to the specific embodiments, but are for explanation and understanding. The drawings are not drawn to scale. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE FIGURES

FIG. 2 illustrates a side view of one embodiment of a treatment device for reducing valve regurgitation prior to deployment, in accordance with the present invention;

FIG. 3 illustrates a side view of the device illustrated in FIG. 2 in a compression configuration;

FIGS. 8 and 9 are side views of a delivery device in accordance with another aspect of the invention; and FIG. 10 is a flowchart illustrating a method for treating cardiac valve regurgitation in accordance with one embodiment of the present invention.

DETAILED DESCRIPTION OF THE PRESENTLY PREFERRED EMBODIMENTS

Figure 1:
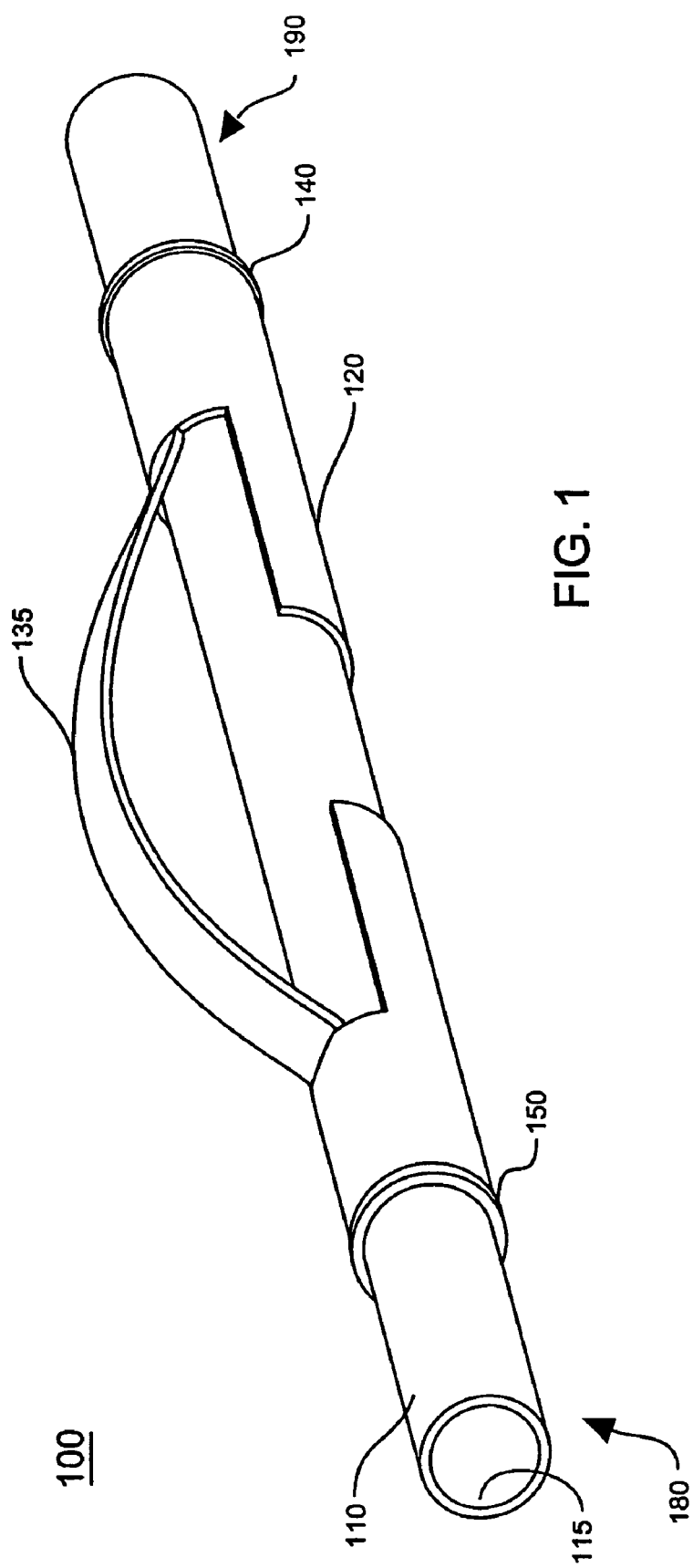
FIG. 1 illustrates a perspective view of one embodiment of a treatment device for reducing valve regurgitation, in accordance with the present invention.

FIG. 1 illustrates a perspective view of one embodiment of a treatment device 100 for reducing valve regurgitation. Treatment device 100 includes an elongated tubular compression device 120 coaxially carried upon tubular member 110. Tubular member 110 includes central lumen 115, locking mechanism 140 and distal stop member 150. Locking mechanism 140 is located adjacent proximal portion 190 of tubular member 110. Distal stop member 150 is located adjacent distal portion 180 of tubular member 110. The terms "distal" and "proximal" are used herein with reference to the treating clinician during deployment of the device; "Distal" indicates a portion distant from, or a direction away from the clinician and "proximal" indicates a portion near to, or direction towards the clinician. Throughout the following description like elements will have like reference numbers as those of FIG. 1.

Referring to FIG. 2, another embodiment of a treatment device for cardiac valves is generally shown at numeral 100. In FIG. 2, treatment device 100 is illustrated in a closed, non-deployed delivery configuration. Treatment device 100 includes elongated tubular compression device 120 coaxially carried upon tubular member 110. Tubular member 110 includes locking mechanism 140 and distal stop member 150. Locking mechanism 140 includes at least one one-way protrusion lock member 142. The at least one lock member 142 and distal stop member 150 are spaced apart along a length L of tubular member 110. Tubular member 110 includes distal portion 180 and proximal portion 190. Tubular member 110 also includes lumen 115 extending there through. Lumen 115 is illustrated as a centrally located co-axial lumen that runs the entire length of tubular member 110 to thereby provide substantially unimpeded flow of blood through the vessel into which it is implanted e.g. the coronary sinus. Those with skill in the art will recognize that lumen 115 may not be co-axial with tubular member 110 though still provide an unimpeded flow of blood.

Compression device 120 includes first segment 122, second segment 124 and compression member 135. Compression member 135 is disposed between and is connected to first segment 122 and second segment 124. In one embodiment, compression member 135 is formed separately from first and second segments 122, 124 and securely attached in a subsequent manufacturing step. Compression member 135 may be attached to first and second segments 122, 124 by welding, adhesive or any other suitable method known to those with skill in the art. In another embodiment, compression member 135 is formed integrally with first and second segments 122, 124.

In one embodiment, first segment 122 and second segment 124 are tubular having an inner diameter sized to freely slide over the outer diameter of tubular member 110. First segment 122 and second segment 124 are composed of axially non-compressible biocompatible metallic or polymeric material or combinations thereof. Compression member 135 comprises stiff elastic material that may transition from a relatively straight, reduced-profile delivery configuration to an arched compression configuration. Compression member 135 may be composed of a biocompatible metal such as nitinol, stainless steel, or cobalt-based alloys. Biocompatible engineering plastics may also be used, such as amides, polyimides, polyolefins, polyesters, urethanes, thermoplastics, thermoset plastics, and blends, laminates or copolymers thereof. In another embodiment, first segment 122 and second segment 124 comprise a stent or stent-like material as are well known in the art.

Lock mechanism 140 includes lock member 142 disposed upon tubular member 110. A proximal portion of second segment 124 may be configured to interact with lock member 142. Generally, lock member 142 is a protrusion along at least a portion of surface 112 of tubular member 110 and is configured to prevent compression device 120 from returning to the delivery configuration once compression device 120 is placed in the compression configuration illustrated in FIG. 3. In one embodiment, lock mechanism 140 comprises a ratchet lock, as are well known in the art, having a plurality of lock members (ratchet teeth) 142 disposed upon surface 112 of tubular member 110 that interact with a ratchet pawl 128 located at proximal end 126 of compression device 120. In another embodiment, lock member 142 is an annular protrusion that encircles tubular member 110 as shown in FIG. 1. In another embodiment, lock mechanism 140 includes one or more rings of ratchet teeth disposed on tubular member 110. In yet another embodiment, lock mechanism 140 includes a plurality of spaced apart rings disposed on tubular member 110. In another embodiment, proximal end 126 of compression device 120 deforms around lock member 142 as proximal end 126 passes over lock member 142 when the device is transforming into the compression configuration. In this embodiment, proximal end 126 returns to a non-deformed configuration that abuts lock member 142 in a locking engagement.

Lock mechanism 140 allows compression device 120 to transform substantially freely from the delivery configuration (FIG. 2) to the compression configuration (FIG. 3) but prevents transformation in the opposite direction. In another embodiment, lock mechanism 140 may be adjustable to allow the physician to increase or decrease the amount of axial compression of compression member 135.

Distal stop member 150 is a protrusion at distal end 114 of tubular member 110 configured to prevent axial movement of compression device 120 beyond stop member 150. In one embodiment, distal stop member 150 is a triangular protrusion configured with a radial portion 152 substantially perpendicular to the axis of compression device 120. As illustrated in FIG. 3, distal end 122 of compression device 120 abuts radial portion 152 to prevent axial movement of compression device 120 beyond distal stop member 150. In another embodiment, distal stop member 150 comprises a stop ring disposed about or integral with tubular member 110. In another embodiment, distal stop member 150 comprises a frustoconical portion of tubular member 110. In another embodiment, distal stop member 150 comprises a portion of compression device 120 that is affixed to tubular member 110.

To deploy the treatment device illustrated in FIGS. 2 and 3, compression device 120 slides along tubular member 110 in response to an applied axial force. In one embodiment, the axial force is applied at proximal end 126 of compression device 120 to bias or push second segment 124 of compression device 120 towards first segment 122. Compression device 120 substantially freely slides over lock member 142.

As compression device 120 is pushed in the distal direction, distal end 123 of first segment 122 abuts distal stop 150 to stop further distal movement of compression device 120. Continued pushing of second segment 124 towards first segment 122 deforms compression member 135 creating the compression configuration as illustrated in FIG. 3. In one embodiment, the compression configuration creates an arched or bowed shape, comprising a radiused portion and increasing the radial distance between compression member 135 and tubular member 110, thus increasing the overall width of treatment device 100 along at least a portion of the length of tubular member 110.

Figure 4:
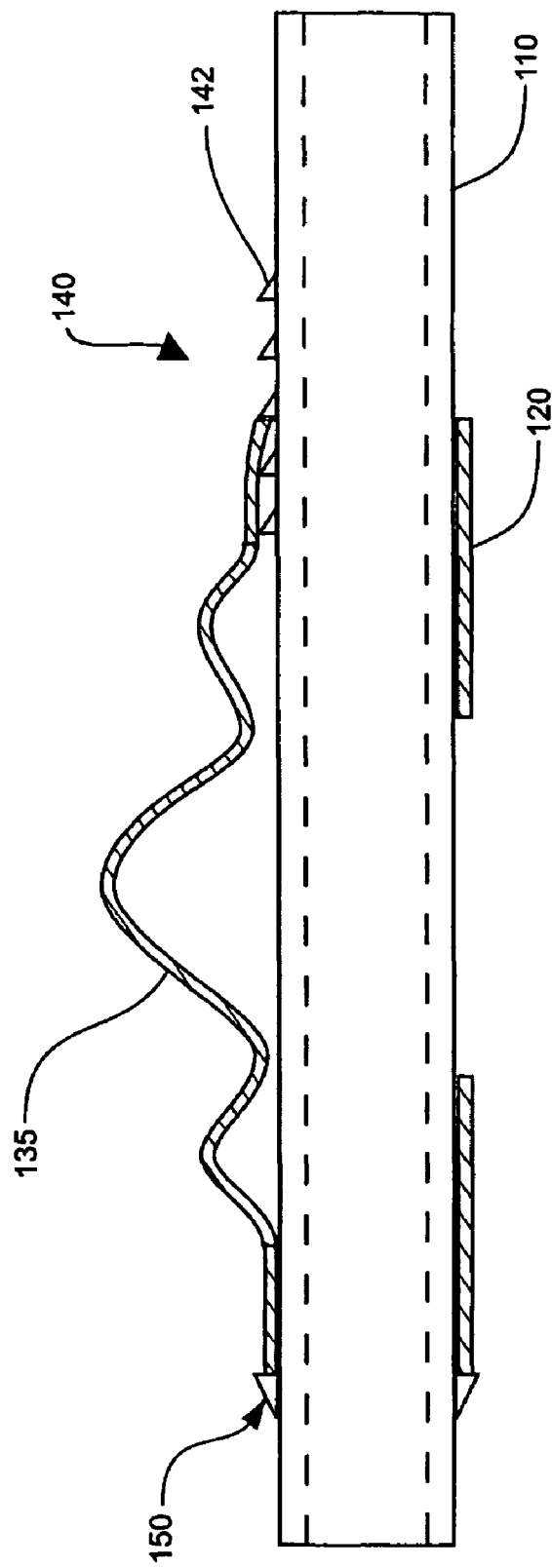
FIG. 4 illustrates a side view of another embodiment of a treatment device for reducing valve regurgitation in the compression configuration, in accordance with the present invention.

FIG. 3 illustrates that compression member 135 assumes a compression configuration comprising a single radially extended portion, forming a generally bowed shape. FIG. 4 illustrates another embodiment of the invention where the compression configuration comprises a series of bowed shapes. In such an embodiment, the compression member 135 comprises a material, including, but not limited to, stainless steel, nitinol, cobalt based alloy, platinum alloy, titanium, a thermoset plastic, or a combination thereof. In another embodiment, compression member 135 is preshaped into the desired compression configuration and is restrained from attaining the compression configuration until allowed to attain such shape in response to axial forces applied to the compression device 120 between lock members 142 and distal stop member 150. In another embodiment, the compression configuration comprises a shape predetermined to interface with an inner wall of the coronary sinus. In yet another embodiment, the compression configuration is predetermined to reduce a natural curved shape of a coronary sinus by straightening the curve.

Figure 5:
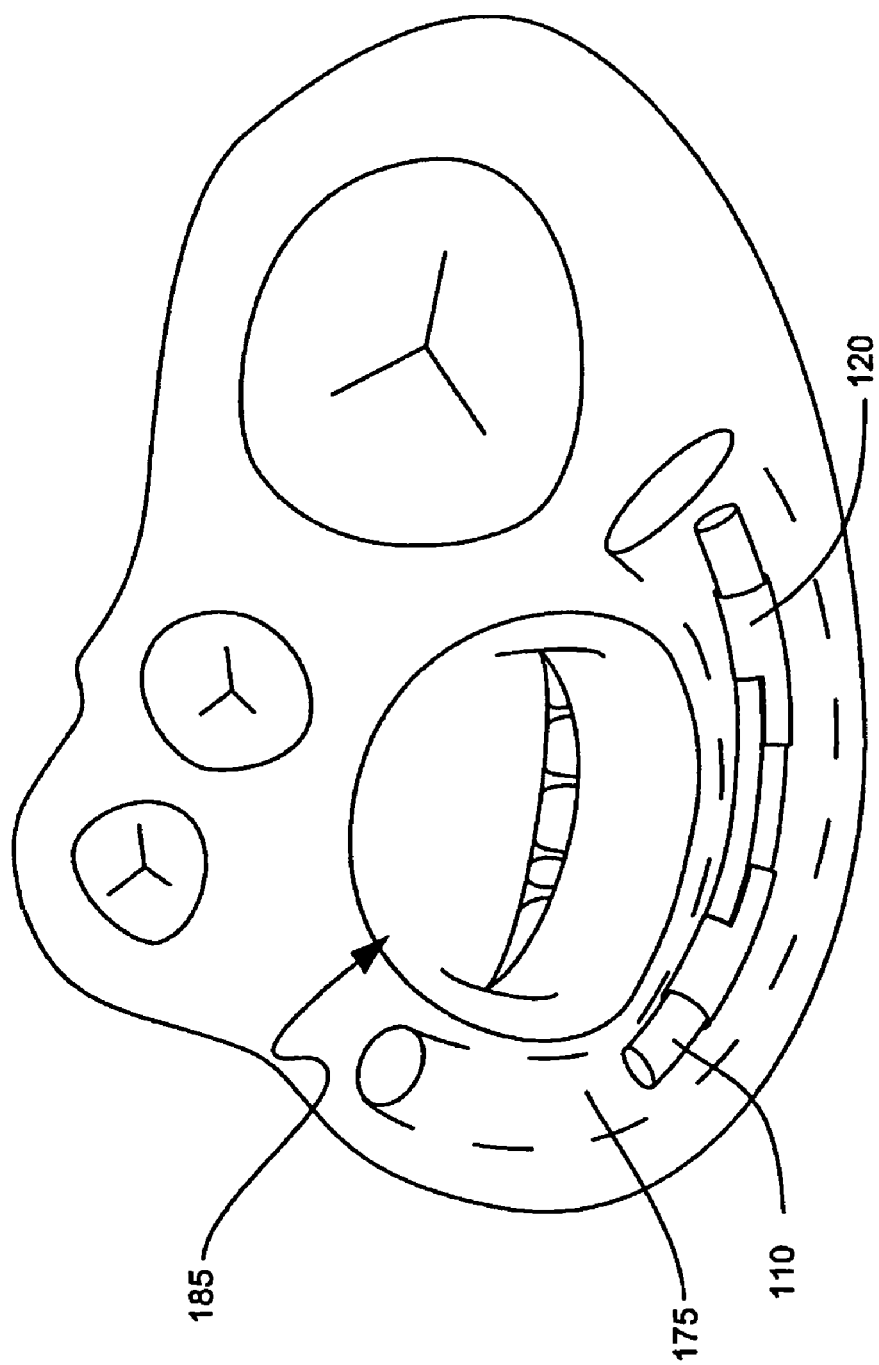
FIG. 5 is an illustration of a treatment device in accordance with the present invention disposed in a coronary sinus prior to deployment adjacent a dilated mitral valve.

FIG. 5 is an illustration of treatment device 100 immediately prior to deployment. Diseased mitral valve 185 is shown incompletely closed, indicating a condition causing mitral valve regurgitation. Coronary sinus 175 lies along the atrioventricular groove on the exterior of the heart proximate mitral valve 185. Compression device 120 and tubular member 110 are shown disposed within coronary sinus 175.

Figure 6:
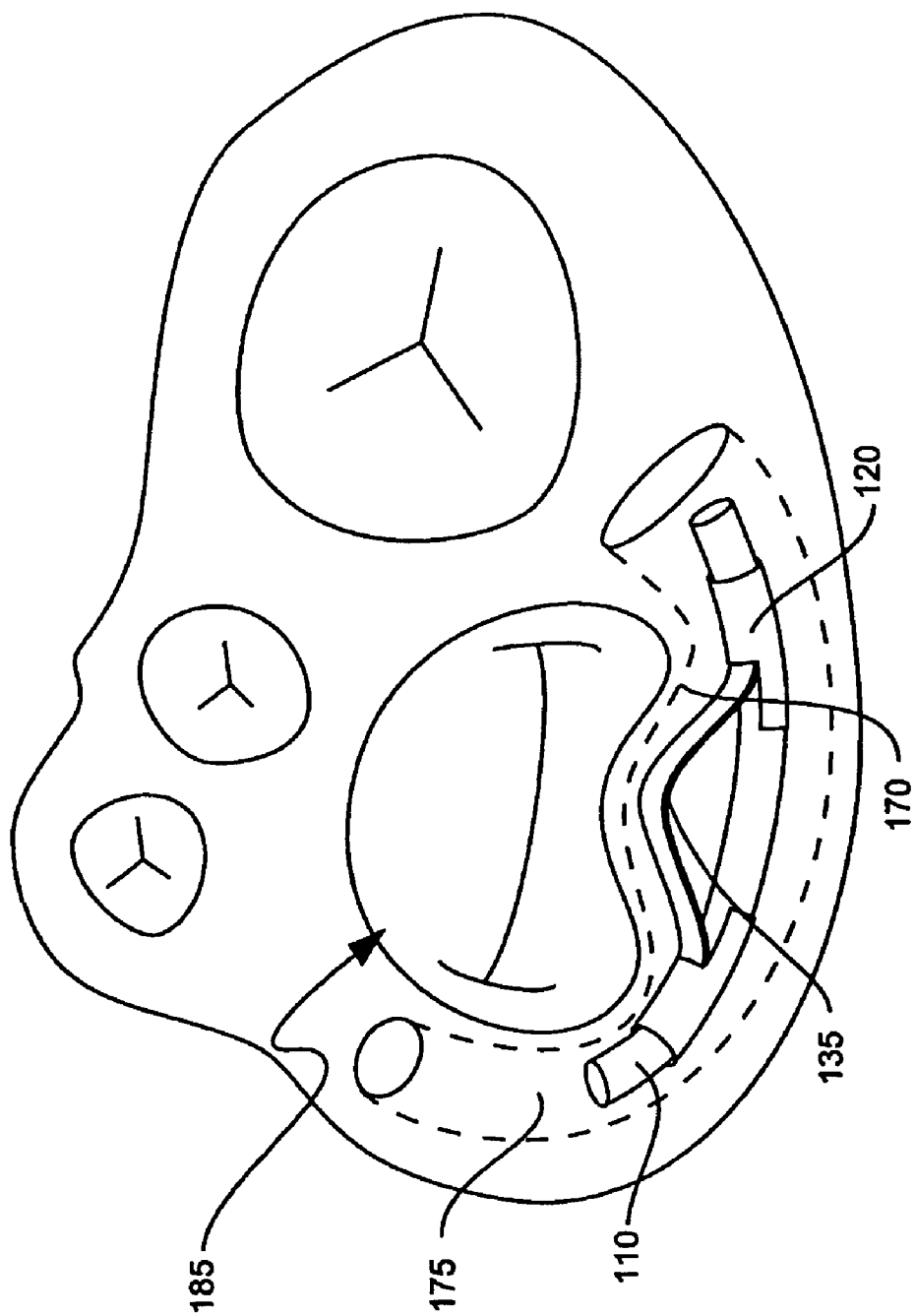
FIG. 6 is an illustration of a treatment device in accordance with the present invention disposed in a coronary sinus after deployment adjacent a mitral valve.

FIG. 6 illustrates treatment device 100, deployed in coronary sinus 175 to a position proximate mitral valve 185. As shown in FIG. 6, the deployed compression device 120 assumes a compression configuration. Upon deployment, compression member 135 extends transversely against a wall of coronary sinus 175 to deform the shape of the coronary sinus and at least a portion of the annulus of mitral valve 185 to allow the valve leaflets to achieve a better seal, and thus reduce mitral valve regurgitation.

FIGS. 5 and 6 also illustrate that treatment device 100 has an outer diameter substantially spanning the inside diameter of the coronary sinus. FIGS. 5 and 6 further illustrate that, when the treatment device is implanted, lumen 115 provides a conduit to maintain blood flow through the coronary sinus substantially equal to the amount of blood flow through the coronary sinus without an implant. The close proximity of compression member 135 to the mitral valve annulus does not require a great deal of radial deflection of compression member 135 to achieve the required change in the mitral valve annulus. Additionally, the close proximity of compression member 135 to the mitral valve annulus allows the clinician to apply a low level of compression to the wall of the coronary sinus in order to affect a change in the mitral valve annulus sufficient to reduce or eliminate valve regurgitation. This ability to apply a reduced amount of pressure to the wall of the coronary sinus substantially decreases the risk of damaging the wall of the coronary sinus.

It is desirable that treatment device 100, 200 be visible during the implantation procedure. The implantation procedure may be visualized using fluoroscopy, echocardiography, intravascular ultrasound, angioscopy, or another means of visualization to aid in positioning. In one embodiment, the surface of each component of treatment device 100, 200, illustrated in FIGS. 1-7, is treated with a substance to enable visualization of the treatment device throughout the implantation procedure. Accurate imaging of the treatment device can ensure the treatment device is delivered as intended by the clinician. Substances to enable imaging of the system are known to those of ordinary skill in the art.

Treatment devices 100, 200 of FIGS. 1-6 may be delivered to the coronary sinus either through surgical access e.g., thoracotomy, port access, or via percutaneous transluminal technique. In one method, the treatment device is delivered transluminally using a catheter based delivery system illustrated in FIG. 7, discussed below. Numerous approaches to deliver a catheter to a position within the coronary sinus are known to those of ordinary skill in the art.

Figure 7:
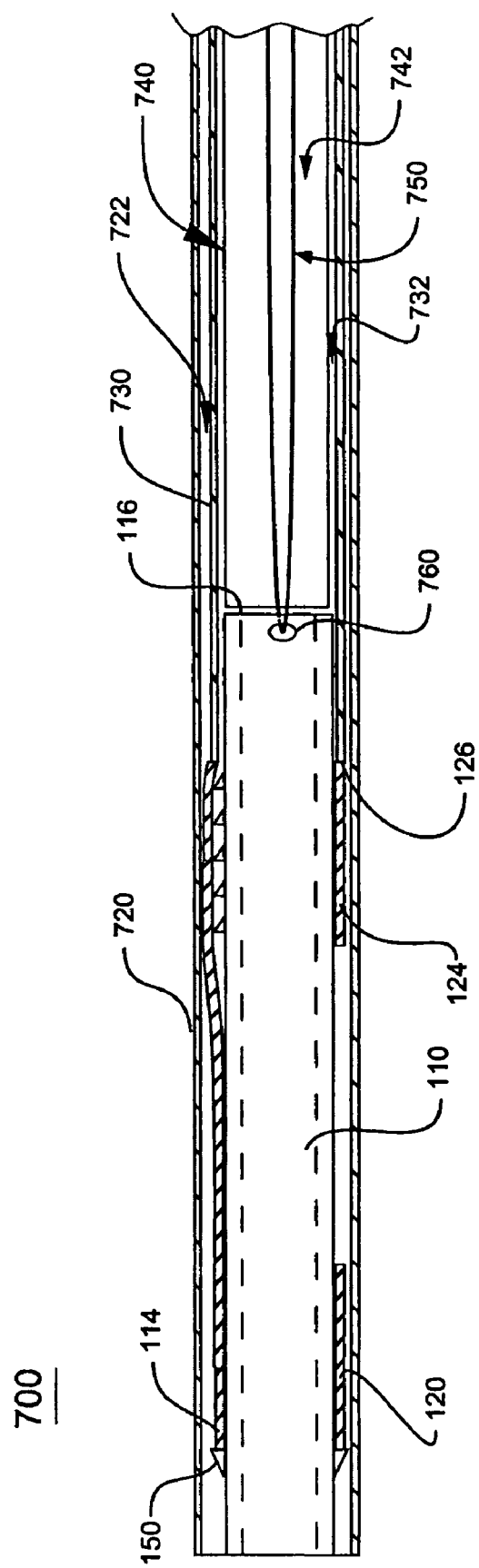
FIG. 7 is a side view of a delivery device in accordance with another aspect of the invention.

FIG. 7 illustrates one embodiment of delivery system 700 in accordance with the invention. FIG. 7 uses like reference numbers for like elements illustrated in FIGS. 1-6. Treatment device 100, 200 illustrated in FIGS. 1-4 is delivered to the desired location within the coronary sinus and is to remain deployed at the delivery site after the end of the deployment procedure. Delivery system 700 comprises delivery catheter 720, push tube 730 and holding tube 740. Holding tube 740 is carried within lumen 732 of push tube 730. Push tube 730 is carried within lumen 722 of delivery catheter 720. Delivery catheter 720 comprises a flexible, biocompatible polymeric material such as polyurethane, polyethylene, nylon, or polytetrafluroethylene (PTFE). Holding tube 740 and push tube 730 also comprise a flexible, biocompatible polymeric material such as polyurethane, polyethylene, nylon, or polytetrafluroethylene (PTFE). Push tube 730 may include a lumen or may be a solid rod of material flexible enough to traverse the vascular pathway to the coronary sinus. Those with skill in the art will recognize that there are other materials or combinations of materials that may be used in the composition of delivery system 700.

Push tube 730 abuts proximal edge 126 of second segment 124 of compression device 120 and is configured to push compression device 120. Holding tube 740 abuts proximal edge 116 of tubular member 110 and is configured to exert axial pressure to tubular member 110.

FIG. 7 further illustrates holding cord 750 disposed within lumen 742 of holding tube 740. Holding cord 750 comprises a string or cord-like material having sufficient length to extend through the patient's vasculature and out of the patient. Holding cord 750 is threaded through hole 760 of tubular member 110 and both ends (not shown) are disposed external to the patient. Holding cord 750 is configured so that the cord may be removed from the vasculature after deployment of treatment device 100, 200 and prior to removal of holding tube 740, push tube 730 and delivery tube 720. Holding cord 750 is configured in such a manner as to maintain contact between holding tube 740 and proximal end 116 of tubular member 110 when pulled in a proximal direction. Holding cord 750, in one embodiment, comprises a tether.

Delivery system 700 illustrated in FIG. 7 is configured so that during delivery, tubular member 110 is maintained in contact with holding tube 740 by holding cord 750. During deployment, push tube 730 exerts pressure on compression device 120 and slides compression device 120 over locking mechanism 140 until distal edge 114 of compression device 120 contacts stop member 150. A desired compression setting is attained by pushing push tube 730 to move compression device 120 in a distal direction and, at the same time, maintaining contact between tubular member 110 and holding tube 740 by holding holding cord 750 in a stationary position. In this manner, a compression configuration is obtained. In one embodiment, to release tubular member 110, holding cord 750 is cut and removed from the vasculature by sliding a free end through the holding tube 740. In another embodiment, a first end of holding cord 750 is released and a second end is pulled until the first end exits the patient's body. Delivery tube 720 is then removed from the vasculature. Compression member 120 remains in the compression configuration upon tubular member 110 within the coronary sinus. Delivery tube 720 may be omitted from delivery system 700 and/or delivery system 700 may be slid over a guidewire.

FIGS. 8 and 9 illustrate another embodiment of a delivery system 800 in accordance with another aspect of the invention. Delivery system 800 comprises push tube 830 slidably disposed upon pull tube 840. Distal end 832 of push tube 830 abuts proximal end 126 of compression device 120. Pull tube 840 includes at least one latch finger 850 at distal end 842 of pull tube 840. Tubular member 110 includes external groove 860 disposed adjacent proximal end 116 of tubular member 110. External groove 860 has a shape complementary to the shape of latch finger 850. In the delivery configuration, latch finger 850 is disposed within external groove 860. Latch finger 850 is pre-formed to be normally splayed open, but during delivery of delivery system 800, latch finger 850 is engaged in external groove 860 and maintained disposed within external groove 860 by push tube 830. Latch finger 850 allows tension or pulling on tubular member 110 when push tube 830 pushes compression device 120 to a compression configuration. Push tube 830 and latch finger 850 may comprise one or more metallic or polymeric biocompatible materials as are known in the catheter art. Upon attaining the desired compression configuration, push tube 830 is pulled back from its distal position to expose latch finger 850. As latch finger 850 is no longer restrained within external groove 860, latch finger 850 splays open and disengages from external groove 860. With latch finger 850 disengaged from external groove 860, the entire delivery system 800 may be removed from the vasculature. FIG. 8 illustrates delivery system 800 prior to disengagement, and FIG. 9 illustrates delivery system 800 after disengagement of latch finger 850 and prior to removal from the vasculature.

FIG. 10 illustrates one embodiment of a method 1000 for treating mitral valve regurgitation using treatment device 100. Method 1000 begins with the delivery of treatment device 100 through the patient's vasculature and into the coronary sinus via delivery system 700 (Block 1010). Treatment device 100 may be delivered by any route suitable for accessing the coronary sinus. Next, compression device 120 is positioned within the coronary sinus adjacent the mitral valve (Block 1020). In one embodiment, delivery catheter 720 is withdrawn to expose treatment device 100. In another embodiment, treatment device 100 is deployed from delivery catheter 720 by distally advancing treatment device 100.

Axial displacement is applied to compression device 120 (Block 1030). A desired compression setting is attained by pushing push tube 730 to push second segment 124 of compression device 120 in a distal direction and, at the same time, maintaining contact between tubular member 110 and holding tube 740 by holding holding cord 750 in a stationary position.

Axial displacement of second segment 124 of compression device 120 transforms compression member 135 into the compression configuration having an extended arched position (Block 1040). In one embodiment, compression member 135 may assume a radially extended position having more than one arch or bow as shown in FIG. 4. Locking mechanism 140 is automatically engaged once compression member 135 is properly transformed into the compression configuration. Treatment device 100 is released after the compression device is locked (Block 1060). In one embodiment, one end of a looped tether is released and the remaining components of the delivery system are retracted and removed from the patient. In another embodiment, push tube 830 is pulled back from its distal position, to expose and release latch finger 850 from external groove 860 thereby disengaging the push tube from treatment device 100 to allow the removal of the delivery system.

Those with skill in the art will recognize that method 1000 may include various other steps not mentioned above. In one embodiment, method 1000 may include hemodynamic monitoring before, during and after the implantation of treatment device 100 in order to monitor the degree to which the implant reduces mitral valve regurgitation. The degree of mitral valve regurgitation may be monitored by techniques such as, transesophageal echo cardiography, surface echo cardiography, intracardiac echo cardiography, or fluoroscopy, as are well known to those with skill in the art.

Other embodiments of treatment device 100, 200 may include additional features depending upon the desired clinical performance. For example, treatment device 100, 200 may be provided with heparin or other antithrombogenic agents. In another or the same embodiment treatment device 100, 200 may include elastomers such as silicone, neoprene, latex or others to soften the surface and reduce the risk of trauma to the coronary sinus wall.

Variations and alterations in the design, manufacture and use of the system and method are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating cardiac valve regurgitation, comprising:
 a delivery catheter;
 a treatment device disposed within a lumen of the delivery catheter;
 the treatment device having a tubular member including a lumen there through and a locking mechanism disposed upon an outer surface of the tubular member, and a compression device carried on the tubular member, the compression device being transformable to a compression configuration responsive to application of an axial displacement and is locked in the compression configuration with the locking mechanism;
 a release mechanism releasably connected to the treatment device;
 the release device having a pull tube slidably disposed within the push tube and having at least one latch finger disposed at a distal end of the pull tube and a groove at a proximal end of the tubular member for receiving the at least one latch finger, wherein the at least one latch finger is held in engagement with the groove by the push tube; and
 a push tube slidably disposed within the delivery catheter for applying an axial force to the treatment device.

2. A system for treating cardiac valve regurgitation, comprising:
   a delivery catheter;
   a treatment device disposed within a lumen of the delivery catheter;
   the treatment device having a tubular member including a lumen there through and a locking mechanism disposed upon an outer surface of the tubular member, and a compression device carried on the tubular member, the compression device being transformable to a compression configuration responsive to application of an axial displacement and is locked in the compression configuration with the locking mechanism;
   a release mechanism releasably connected to the treatment device;
   the release device having a pull tube slidably disposed within the push tube and having at least one latch finger disposed at a distal end of the pull tube, and a groove at a proximal end of the tubular member for receiving the at least one latch finger, wherein the at least one latch finger is held in engagement with the groove by the push tube and is released from the groove by sliding the push tube over the pull tube to expose the at least one latch finger and
   a push tube slidably disposed within the delivery catheter for applying an axial force to the treatment device.

3. The system of claim 1 wherein the compression device comprises a compression member disposed between a first segment and a second segment.

4. The system of claim 3 wherein the compression member comprises a metal selected from the group consisting of nitinol, stainless steel, and cobalt-based alloys, or a plastic selected from the group consisting of amides, polyimides, polyolefins, polyesters, urethanes, thermoplastics, thermoset plastics, blends thereof, and copolymers thereof.

5. The system of claim 3 wherein the first segment and the second segment each comprise a tubular shape composed of an axially incompressible material.

6. The system of claim 1 wherein the locking mechanism comprises a stop member spaced apart from at least one lock member along a length of the tubular member.

7. The system of claim 6 wherein the lock member comprises a one-way protrusion lock member.

8. The system of claim 1 wherein the compression device comprises at least one radially extendable compression member.

9. The system of claim 8 wherein the compression member comprises a self-expanding member having a predetermined deployment shape to interface with an interior wall of a vessel.

10. The system of claim 1 wherein the release mechanism further comprises a looped tether releasably connected to the tubular member.

* * * * *